(12) United States Patent
Ooshima et al.

(10) Patent No.: US 10,373,889 B2
(45) Date of Patent: Aug. 6, 2019

(54) ELECTRONIC DEVICE AND METHOD OF MANUFACTURING THE SAME

(71) Applicant: DENSO CORPORATION, Kariya, Aichi-pref. (JP)

(72) Inventors: Masanori Ooshima, Kariya (JP); Eiji Hayashi, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 16/079,128

(22) PCT Filed: Mar. 24, 2017

(86) PCT No.: PCT/JP2017/011948
§ 371 (c)(1),
(2) Date: Aug. 23, 2018

(87) PCT Pub. No.: WO2017/179394
PCT Pub. Date: Oct. 19, 2017

(65) Prior Publication Data
US 2019/0057921 A1    Feb. 21, 2019

(30) Foreign Application Priority Data

Apr. 13, 2016 (JP) ................. 2016-080578

(51) Int. Cl.
*H01L 21/56* (2006.01)
*H01L 25/065* (2006.01)
(Continued)

(52) U.S. Cl.
CPC ......... *H01L 23/3142* (2013.01); *G01N 29/04* (2013.01); *H01L 21/4803* (2013.01);
(Continued)

(58) Field of Classification Search
CPC ... G01N 29/04; H01L 23/28–29; H01L 23/48; H01L 23/49537; H01L 23/49568;
(Continued)

(56) References Cited

U.S. PATENT DOCUMENTS

2013/0078423 A1* 3/2013 Sutou ................ B29C 45/14311
428/141
2014/0305914 A1    10/2014 Sutou et al.

FOREIGN PATENT DOCUMENTS

JP    H07-115170 A    5/1995
JP    2001-225346 A    8/2001
(Continued)

*Primary Examiner* — Daniel P Shook
(74) *Attorney, Agent, or Firm* — Posz Law Group, PLC

(57) ABSTRACT

In an electronic device including an electronic component, a sealing resin body, a first member having at least a portion located in the sealing resin body, and a second member connected to the first member via a solder in the sealing resin body, the first member includes a base material formed of a metal material and a coated film at least on a surface of the base material which is adjacent to a back surface of the first member opposite to a facing surface of the first member facing the second member. The coated film includes a metal thin film on a surface of the base material and an uneven oxide film on the metal thin film and made of an oxide of a same metal as a main component of the metal thin film.

10 Claims, 8 Drawing Sheets

(51) Int. Cl.
- *G01N 29/04* (2006.01)
- *H01L 21/48* (2006.01)
- *H01L 23/00* (2006.01)
- *H01L 23/28* (2006.01)
- *H01L 23/29* (2006.01)
- *H01L 23/31* (2006.01)
- *H01L 23/48* (2006.01)
- *H01L 23/50* (2006.01)
- *H01L 25/07* (2006.01)
- *H01L 25/18* (2006.01)
- *H01L 23/495* (2006.01)

(52) U.S. Cl.
CPC .......... *H01L 21/4825* (2013.01); *H01L 21/56* (2013.01); *H01L 23/28* (2013.01); *H01L 23/29* (2013.01); *H01L 23/48* (2013.01); *H01L 23/49537* (2013.01); *H01L 23/49562* (2013.01); *H01L 23/49568* (2013.01); *H01L 23/49575* (2013.01); *H01L 23/49582* (2013.01); *H01L 23/49586* (2013.01); *H01L 23/50* (2013.01); *H01L 24/32* (2013.01); *H01L 24/33* (2013.01); *H01L 25/0655* (2013.01); *H01L 25/07* (2013.01); *H01L 25/18* (2013.01); *G01N 2291/267* (2013.01); *H01L 23/49551* (2013.01); *H01L 2224/32245* (2013.01); *H01L 2224/33* (2013.01); *H01L 2224/33181* (2013.01); *H01L 2224/48247* (2013.01); *H01L 2924/14252* (2013.01); *H01L 2924/181* (2013.01)

(58) Field of Classification Search
CPC ......... H01L 23/49575; H01L 23/49582; H01L 23/49586; H01L 25/07; H01L 25/18
See application file for complete search history.

(56) References Cited

FOREIGN PATENT DOCUMENTS

| | | |
|---|---|---|
| JP | 4968195 B2 | 7/2012 |
| JP | 2013-251500 A | 12/2013 |
| JP | 2014-117724 A | 6/2014 |

* cited by examiner

ELECTRONIC DEVICE AND METHOD OF MANUFACTURING THE SAME

CROSS REFERENCE TO RELATED APPLICATIONS

This application is a U.S. national stage application of International Application No. PCT/JP2017/011948 filed on Mar. 24, 2017 and is based on Japanese Patent Application No. 2016-80578 filed on Apr. 13, 2016, the disclosures of which are incorporated herein by reference.

TECHNICAL FIELD

The present disclosure relates to a resin-sealed electronic device and a method of manufacturing the same.

BACKGROUND

There has conventionally been known a resin-sealed electronic device including an electronic component, a sealing resin body sealing the electronic component, a first member having at least a portion located in the sealing resin body, and a second member connected to the first member via a solder in the sealing resin body.

In such an electronic device, after the sealing resin body is molded, using a supersonic flaw detector (SAT: Scanning Acoustic Tomograph), the solder is inspected from the first member side in the stacking direction in which the first member, the solder, and the second member are stacked. Specifically, a void in the solder or the like is inspected. The first member has a facing surface facing the second member and a back surface opposite to the facing surface, and the facing surface includes a connection region which is connected to the solder. When the peeling of the sealing resin body occurs at the portion of the back surface of the first member which overlaps the connection region of the facing surface in a projected view along the stacking direction, a supersonic wave is reflected by each of the interface between the sealing resin body and air and the interface between the air and the first member. Consequently, the solder cannot be inspected with high accuracy.

On the other hand, as disclosed in Patent Literature 1, a technique is known which roughens the surface of a metal member and restricts a sealing resin body from peeling from the surface of the metal member using the resulting anchoring effect exerted on the sealing resin body.

PRIOR ART LITERATURE

Patent Literature

Patent Literature 1: JP 2013-71312 A

SUMMARY

However, in the conventional technique described above, the back surface portion of the connection region of the first member which is connected to the solder may be corroded. For example, the metal member is corroded by a chlorine-based compound remaining in the sealing resin body. In addition, when moisture comes in from the outside through the interface between the sealing resin body and the first member or the like, the metal member is corroded. When corrosion has thus occurred, even when the metal surface is roughened, the peeling of the sealing resin body occurs. In other words, the solder cannot be inspected with high accuracy using the supersonic flaw detector.

An object of the present disclosure is to provide an electronic device which allows a solder to be detected with high accuracy using a supersonic flaw detector and a method of manufacturing the same.

According to a first aspect of the present disclosure, an electronic device includes: an electronic component; a sealing resin body sealing the electronic component; a first member having at least a portion located in the sealing resin body; and a second member connected to the first member via a solder in the sealing resin body. The first member has a facing surface facing the second member and a back surface opposite to the facing surface. The first member includes a base material formed of a metal material and a coated film provided at least on a surface of the base material which is adjacent to the back surface of the first member. The coated film includes a metal thin film provided on the surface of the base material and an uneven oxide film provided on the metal thin film and made of an oxide of a metal that is a same metal as a main component of the metal thin film. The uneven oxide film is provided in the back surface of the first member so as to overlap at least an entirety of a connection region of the facing surface of the first member which is connected to the solder in a projected view along a stacking direction in which the first member, the solder, and the second member are stacked.

In accordance with the first aspect, on a back surface portion of the first member, which is on the back surface and corresponds to the connection region connected to the solder, the uneven oxide film is formed. The uneven oxide film has a surface with consecutive depressions and projections and, due to an anchoring effect and the effect of an increased contact area, it is possible to restrict the peeling of the sealing resin body. As a result, it is possible to inspect the solder with high accuracy through the first member by a supersonic flaw inspection.

In addition, since the uneven oxide film is formed on the metal thin film, the uneven oxide film can prevent the corrosion of the first member. Consequently, it is possible to restrict the peeling of the sealing resin body resulting from corrosion and inspect the solder with high accuracy by the supersonic flaw inspection. Note that, as will be described later, the uneven oxide film is formed by irradiating the metal thin film with a pulse oscillation laser beam.

According to a second aspect of the present disclosure, a method is for manufacturing an electronic device including: an electronic component; a sealing resin body sealing the electronic component; a first member having at least a portion located in the sealing resin body; and a second member connected to the first member via a solder in the sealing resin body. In the electronic device, the first member includes a base material formed of a metal material and a coated film provided at least on a surface of the base material which is adjacent to a back surface of the first member opposite to a facing surface of the first member facing the second member. The coated film includes a metal thin film provided on the surface of the base material and an uneven oxide film provided on the metal thin film and made of an oxide of a metal that is a same metal as a main component of the metal thin film. The uneven oxide film is provided in the back surface of the first member so as to overlap at least an entirety of a connection region of the facing surface of the first member which is connected to the solder in a projected view along a stacking direction in which the first member, the solder, and the second member are stacked. The method includes: preparing the base material formed with the metal thin film; forming the uneven oxide film by irradiating a surface of the metal thin film on the back surface of the first member with a pulse oscillation laser beam, the surface of the metal think film irradiated including at least a portion that corresponds to an entire region of the connection region; connecting the first member and the second member via the solder; molding the sealing resin body, after the forming of the uneven oxide film and the connecting of the first member and the second member; and inspecting the solder from a side adjacent to the first member in the stacking direction using a supersonic flaw detector after the molding of the sealing resin body.

In accordance with the second aspect, by irradiating the metal thin film with a pulse oscillation laser beam, it is possible to form the uneven oxide film having a surface with consecutive depressions and projections. Accordingly, in the same manner as described above, it is possible to restrict the sealing resin body from peeling from the back surface portion of the connection region of the first member. This allows the solder to be inspected with high accuracy from the first member side by a supersonic flaw inspection.

In addition, since the uneven oxide film is formed over the metal thin film, the uneven oxide film can prevent the corrosion of the first member. As a result, it is possible to restrict the peeling of the sealing resin body resulting from corrosion and inspect the solder with high accuracy by the supersonic flaw inspection.

BRIEF DESCRIPTION OF DRAWINGS

The above and other objects, features and advantages of the present disclosure will become more apparent from the following detailed description made with reference to the accompanying drawings, in which.

DETAILED DESCRIPTION

Figure 1:
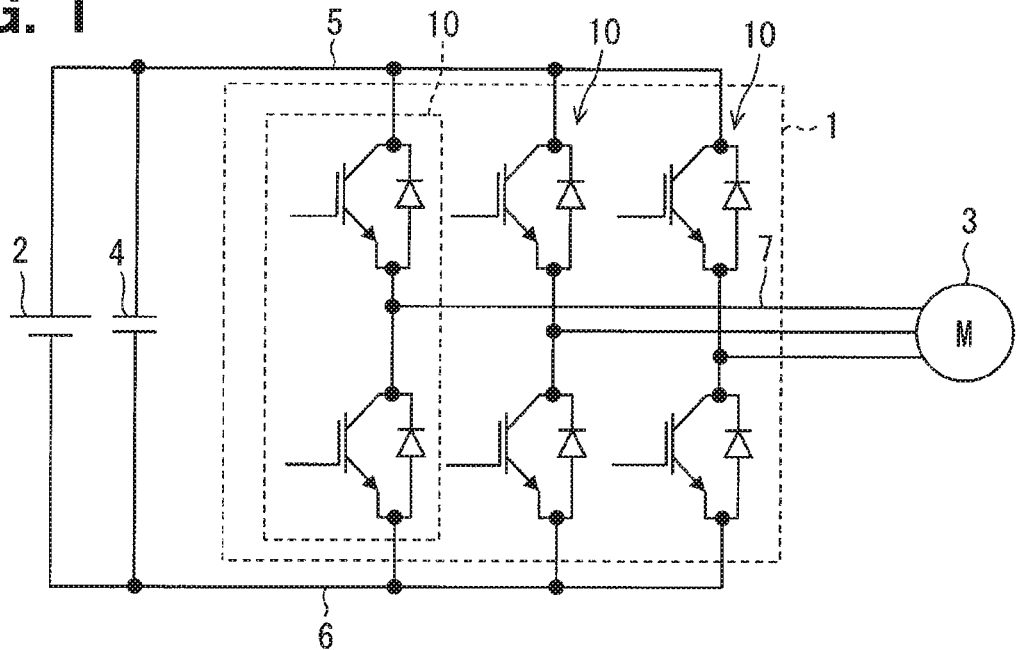
FIG. 1 is a view showing a schematic configuration of a power conversion device to which a semiconductor device according to a first embodiment is applied.

Referring to the drawings, a plurality of embodiments will be described. In the plurality of embodiments, functionally and/or structurally corresponding parts are given the same reference numerals. In the following description, a thickness direction of each of semiconductor chips is shown as a Z-direction, and a direction which is orthogonal to the Z-direction and in which the two semiconductor chips are arranged is shown as an X-direction. Also, a direction orthogonal to both of the Z-direction and the X-direction is shown as a Y-direction. Also, a shape along an XY-plane defined by the X-direction and the Y-direction each described above is referred to as a planar shape unless particularly described otherwise.

First Embodiment

First, on the basis of FIG. 1, a description will be given of an example of a power conversion device to which a semiconductor device is applied.

A power conversion device 1 shown in FIG. 1 is configured so as to convert a DC voltage supplied from a DC power source 2 (battery) to a three-phase AC current and output the three-phase AC current to a three-phase AC motor 3. The power conversion device 1 thus configured is mounted in, e.g., an electric automobile or a hybrid car. Note that the power conversion device 1 can also convert the power generated by the motor 3 to a DC power and charge the DC power source 2 with the DC power. The reference numeral 4 shown in FIG. 2 denotes a smoothing capacitor.

The power conversion device 1 has a three-phase inverter. The three-phase inverter has upper and lower arms corresponding to three phases which are provided between a higher-potential power source line 5 connected to the positive (higher-potential) electrode of the DC power source 2 and a lower-potential power source line 6 connected to the negative (lower-potential) electrode of the DC power source 2. The upper and lower arms in each of the phases are formed of one of semiconductor devices 10. That is, each of the semiconductor devices 10 forms the upper and lower arms corresponding to one of the phases.

Each of the semiconductor devices 10 includes IGBT elements and back-flow FWD elements connected in anti-parallel to the IGBT elements. In the present embodiment, the IGBT element and the FWD element are formed in each of semiconductor chips 12 described later. However, the IGBT element and the FWD element may also be formed in different chips. In the present embodiment, the n-channel IGBT elements are used. The cathode electrode of each of the FWD elements is used also as a collector electrode, and the anode electrode of the FWD element is used also as an emitter electrode.

In the semiconductor devices 10, the collector electrodes of the upper-arm IGBT elements are electrically connected to the higher-potential power source line 5, while the emitter electrodes of the upper-arm IGBT elements are connected to an output line 7 to the motor 3. On the other hand, the collector electrodes of the lower-arm IGBT elements are connected to the output line 7 to the motor 3, while the emitter electrodes of the lower-arm IGBT elements are electrically connected to the lower-potential power source line 6.

Note that the power conversion device 1 may also include, in addition to the three-phase inverter described above, a boosting converter which boosts the DC voltage supplied from the DC power source 2 and a control unit which controls the operation of each of the switching elements forming the three-phase inverter and the boosting converter.

Next, on the basis of FIGS. 2 to 7, a description will be given of a schematic configuration of the semiconductor device 10.

As shown in FIGS. 2 to 7, the semiconductor device 10 includes a sealing resin body 11, the semiconductor chips 12, first heat sinks 14, terminals 17, second heat sinks 19, main terminals 23, 24, and 25, and signal terminals 26. The semiconductor device 10 corresponds to a resin-sealed electronic device. In the following description, H at the end of each of reference numerals shows that the element denoted thereby is an upper-arm element, while L at the end of each of reference numerals shows that the element denoted thereby is a lower-arm element. Some of elements are denoted by reference numerals having additional H's and L's at the ends thereof to clearly show that the elements are the upper- and lower-arm elements, while others of the elements are denoted by common reference numerals denoting both the upper-arm elements and the lower-arm elements.

Figure 2:
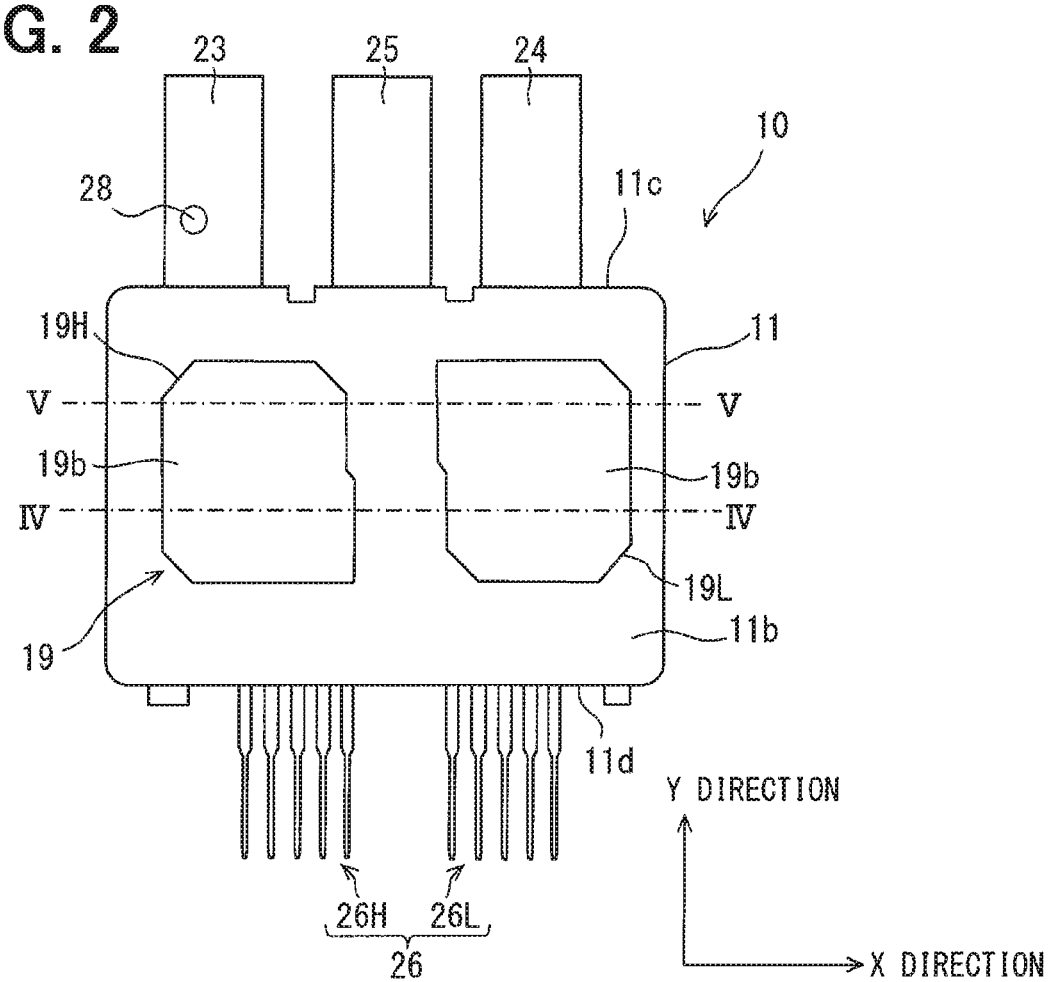
FIG. 2 is a plan view showing a schematic configuration of the semiconductor device according to the first embodiment.
Figure 4:
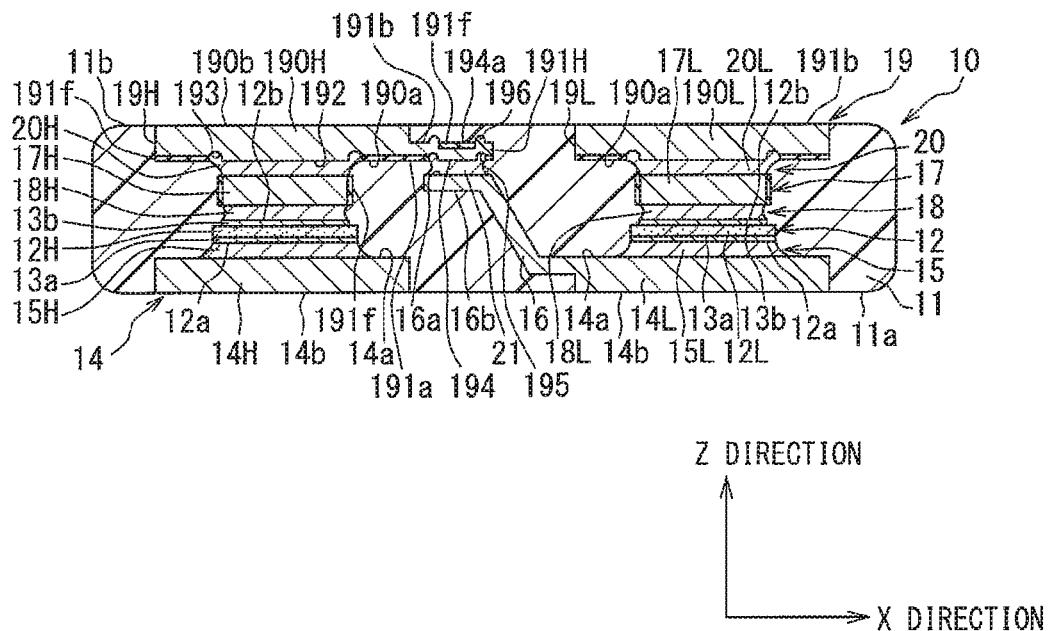
FIG. 4 is a cross-sectional view along the line IV-IV in FIG. 2.
Figure 5:
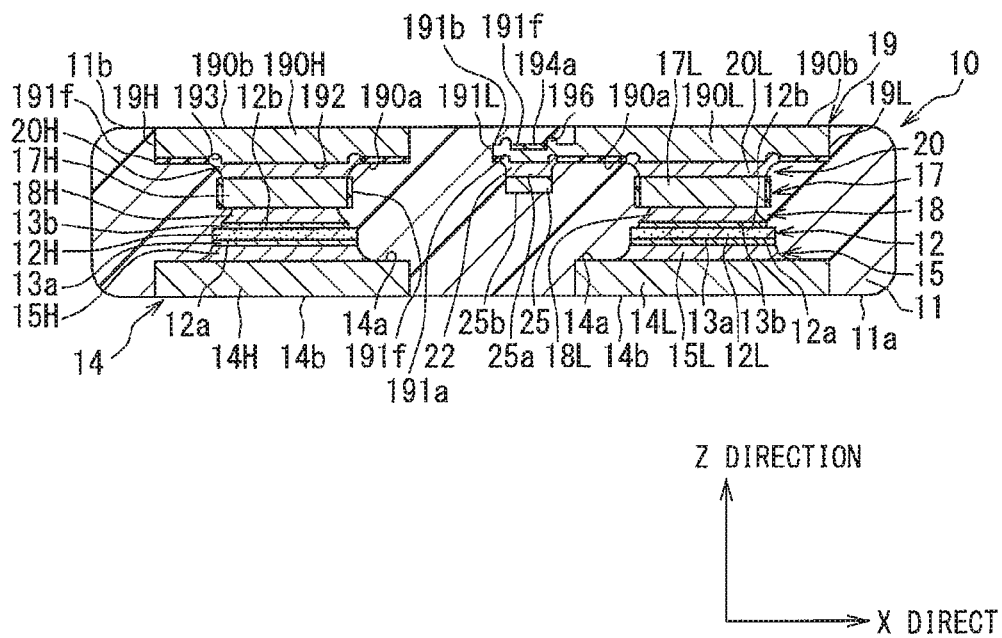
FIG. 5 is a cross-sectional view along the line V-V in FIG. 2.

The sealing resin body 11 is made of, e.g., an epoxy-based resin. The sealing resin body 11 has a generally rectangular shape as a planar shape. As shown in FIGS. 2, 4, and 5, the sealing resin body 11 has a one surface 11a orthogonal to the Z-direction, a back surface 11b opposite to the one surface 11a, and side surfaces connecting the one surface 11a with the back surface 11b. The one surface 11a and the back surface 11b are, e.g., planar surfaces. The sealing resin body 11 has, as the side surfaces thereof, a side surface 11c from which the main terminals 23 and 24 protrude and a side surface 11d from which the signal terminals 26 protrude.

Each of the semiconductor chips 12 includes a semiconductor substrate made of silicon or the like and a power transistor, such as an insulated-gate bipolar transistor (IGBT), formed in the substrate. In the present embodiment, an n-channel IGBT and a flywheel diode (FWD) connected in anti-parallel to the IGBT are formed. That is, in the semiconductor chip 12, an RC (Reverse Conducting)-IGBT is formed. The semiconductor chip 12 has a generally rectangular shape as a planar shape.

The IGBT and the FWD have a vertical structure to allow a current to flow in the Z-direction. As shown in FIGS. 4 and 5, in the thickness direction of each of the semiconductor chips 12, i.e., in the Z-direction, a collector electrode 13a is formed on a one surface 12a, while an emitter electrode 13b is formed on a back surface 12b opposite to the one surface 12a. The collector electrode 13a serves also as the cathode electrode of the FWD, while the emitter electrode 13b serves also as the anode electrode of the FWD. On the back surface 12b of the semiconductor chip 12, i.e., the surface thereof where the emitter electrode is formed, pads including a pad for a gate electrode and not shown are formed. The semiconductor chip 12 corresponds to an electronic component.

The semiconductor chips 12 include an upper-arm semiconductor chip 12H and a lower-arm semiconductor chip 12L. The semiconductor chips 12H and 12L have substantially the same planar shapes, specifically, generally rectangular shape as the planar shape. Also, the semiconductor chips 12H and 12L have substantially the same sizes, and substantially the same thicknesses. The semiconductor chips 12H and 12L are disposed such that the respective collector electrodes 13a thereof are on the same side of the semiconductor chips 12H and 12L in the Z-direction, and the respective emitter electrodes 13b thereof are on the same side of the semiconductor chips 12H and 12L in the Z-direction. The semiconductor chips 12H and 12L are disposed at substantially the same heights in the Z-direction, while being arranged side by side in the X-direction. The semiconductor chip 12H corresponds to the upper-arm chip, while the semiconductor chip 12L corresponds to the lower-arm chip. The X-direction in which the semiconductor chips 12H and 12L are arranged corresponds to an orthogonal direction.

Each of the first heat sinks 14 has the function of dissipating heat in the corresponding semiconductor chip 12 to the outside of the semiconductor device 10 and also has the function of a wire. Accordingly, to ensure a thermal conductivity and an electrical conductivity, the first heat sink 14 is formed using at least a metal material. The first heat sink 14 is referred to also as a heat dissipation member. In the present embodiment, the first heat sink 14 is provided so as to include the corresponding semiconductor chip 12 in a projected view along the Z-direction.

Each of the first heat sinks 14 includes a facing surface 14a facing the one surface 12a of the semiconductor chip 12 and a heat dissipation surface 14b opposite to the facing surface 14a. The facing surface 14a of the first heat sink 14 and the collector electrode 13a of the semiconductor chip 12 corresponding to the first heat sink 14 are electrically connected via a solder 15. The major part of the first heat sink 14 is covered with the sealing resin body 11. The facing surface 14a is located in the sealing resin body 11, while the heat dissipation surface 14b is exposed from the sealing resin body 11. The heat dissipation surface 14b is generally flush with the one surface 11a of the sealing resin body 11.

In the present embodiment, the first heat sinks 14 include an upper-arm first heat sink 14H and a lower-arm first heat sink 14L. Also, the solders 15 include an upper-arm solder 15H and a lower-arm solder 15L. The first heat sink 14H is connected to the collector electrode 13a of the semiconductor chip 12H via the solder 15H. On the other hand, the first heat sink 14L is connected to the collector electrode 13a of the semiconductor chip 12L via the solder 15L. The first heat sinks 14H and 14L are disposed to be arranged in the X-direction, while being disposed at substantially the same positions in the Z-direction. The respective heat dissipation surfaces 14b of the first heat sinks 14H and 14L are exposed from the one surface 11a of the sealing resin body 11, while being arranged in the X-direction.

Figure 3:
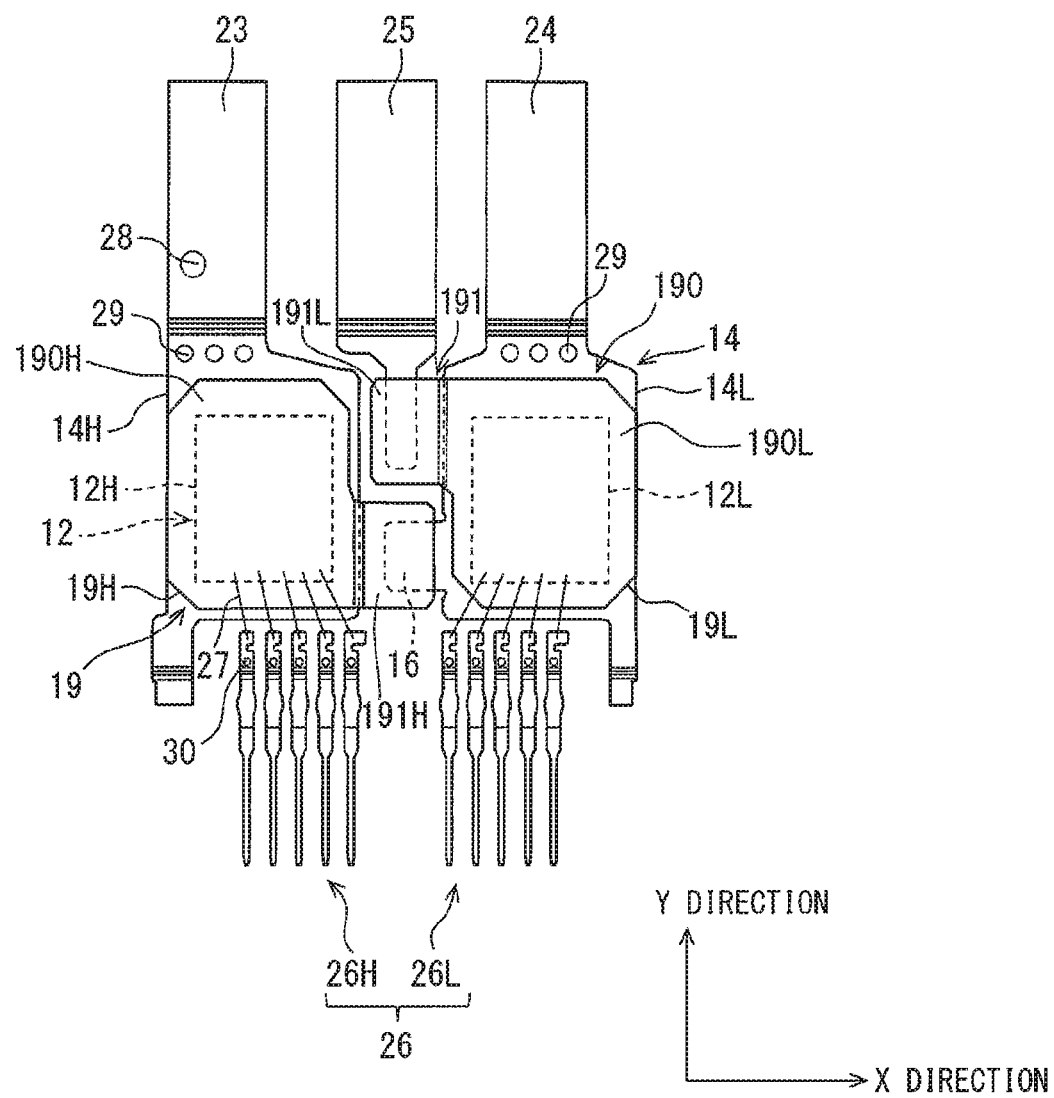
FIG. 3 is a view of the semiconductor device shown in FIG. 2 from which a sealing resin body is omitted.

As shown in FIGS. 3 and 4, a joint part 16 is continued to the lower-arm first heat sink 14L. The joint part 16 is the part serving as an electrical relay between the first heat sink 14L and a second heat sink 19H described later. In the present embodiment, the joint part 16 is provided integrally with the first heat sink 14L by processing the same metal plate. Consequently, the joint part 16 is a part of the first heat sink 14L. The joint part 16 is continued to the main body part of the first heat sink 14L which is connected to the semiconductor chip 12L via the solder 15H.

The joint part 16 is provided thinner than the first heat sink 14L so as to be covered with the sealing resin body 11. The joint part 16 is continued to the first heat sink 14L to be generally flush with the facing surface 14a of the first heat sink 14L. The joint part 16 extends from around one end of the first heat sink 14L in the Y-direction toward the second heat sink 19H. In the present embodiment, as shown in FIG. 4, the joint part 16 has two bent parts. The joint part 16 corresponds to a second member.

Each of the terminals 17 is interposed between the corresponding semiconductor chip 12 and the corresponding second heat sink 19. The terminal 17, which is located at a middle in a thermal/electrical conduction path between the semiconductor chip 12 and the second heat sink 19, is formed using at least a metal material (e.g., Cu) so as to ensure a thermal conductivity and an electrical conductivity. The terminal 17 in the present embodiment has a base material formed using Cu and a metal thin film containing Ni as a main component and formed on the surface of the base material. The terminal 17 is disposed to face the emitter electrode 13b and electrically connected to the emitter electrode 13b via a solder 18.

In the present embodiment, the terminals 17 include an upper-arm terminal 17H and a lower-arm terminal 17L. Also, the solders 18 include an upper-arm solder 18H and a lower-arm solder 18L. The terminal 17H is connected to the emitter electrode 13b of the semiconductor chip 12H via the solder 18H. The terminal 17L is connected to the emitter electrode 13b of the semiconductor chip 12L via the solder 18L.

Each of the second heat sinks 19 has the function of dissipating heat in the corresponding semiconductor chip 12 to the outside of the semiconductor device 10 and also has the function of a wire. Accordingly, to ensure a thermal conductivity and an electrical conductivity, the second heat sink 19 is formed using at least a metal material, similarly to the first heat sink 14. The second heat sink 19 is referred to also as a heat dissipation member. In the present embodiment, the second heat sink 19 is provided so as to include the corresponding semiconductor chip 12 in a projected view along the Z-direction.

Figure 6:
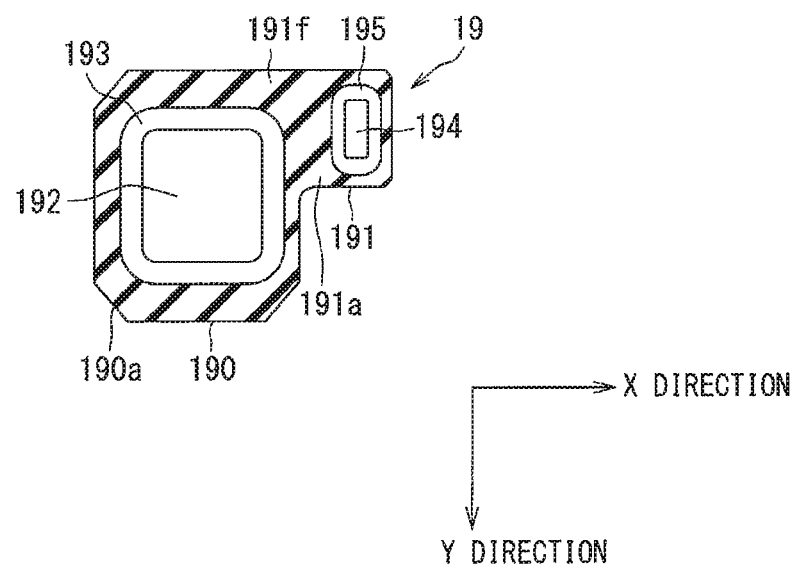
FIG. 6 is a plan view in which a second heat sink is viewed from a facing surface side.
Figure 7:
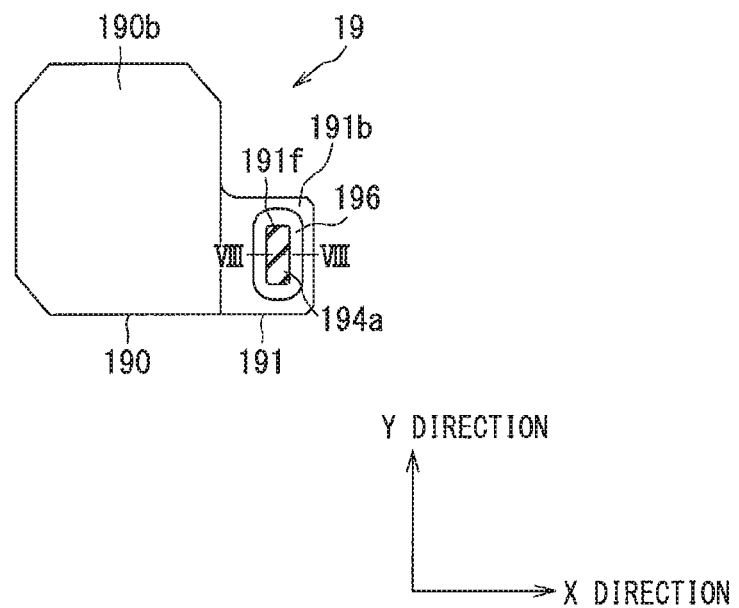
FIG. 7 is a plan view in which the second heat sink is viewed from a heat dissipation surface side.

As shown in FIGS. 3, 6, and 7, each of the second heat sinks 19 has a generally L-shape as a planar shape and includes a main body part 190 and an extending part 191 extending from the main body part 190. In FIGS. 6 and 7, the second heat sink 19H described later is shown by way of example as the second heat sink 19.

The main body part 190 has a facing surface 190a facing the corresponding terminal 17 and a heat dissipation surface 190b opposite to the facing surface 190a. The facing surface 190a of the second heat sink 19 and the corresponding terminal 17 are electrically connected via a solder 20. The major part of the main body part 190 is covered with the sealing resin body 11. The facing surface 190a is located in the sealing resin body 11, while the heat dissipation surface 190b is exposed from the sealing resin body 11. Specifically, the heat dissipation surface 190b and the back surface 11b of the sealing resin body 11 are generally flush with each other.

The extending part 191 is provided integrally with the main body part 190 by processing the same metal plate. The extending part 191 is provided thinner than the main body part 190 so as to be covered with the sealing resin body 11. The extending part 191 has a facing surface 191a facing either of the joint part 16 and the main terminal 25 and a back surface 191b opposite to the facing surface 191a. The extending part 191 is continued to the main body part 190 such that the facing surfaces 190a and 191a are flush with each other. The second heat sink 19 is disposed such that the extending direction of the extending part 191 extends along the X-direction.

In the present embodiment, the second heat sinks 19 include the upper-arm second heat sink 19H and a lower-arm second heat sink 19L, and the solders 20 include an upper-arm solder 20H and a lower-arm solder 20L. Also, the main body parts 190 include an upper-arm main body part 190H and a lower-arm main-body part 190L, and the extending parts 191 include an upper-arm extending part 191H and a lower-arm extending part 191L.

As shown in FIGS. 3, 6, and 7, the second heat sinks 19H and 19L have the same shape. The second heat sink 19H and the second heat sink 19L are disposed so as to achieve two-fold symmetry. In addition, the two second heat sinks 19H and 19L are disposed such that, in the X-direction, the extending part 191H faces the main body part 190L, and the extending part 191L faces the main body part 190H. In other words, the two second heat sinks 19H and 19L are disposed such that the extending parts 191H and 191L are arranged side by side in the Y-direction.

In such a layout, the main body part 190H of the second heat sink 19H and the terminal 17H are connected via the solder 20H. Consequently, the semiconductor chip 12H is fixed to the second heat sink 19H via the terminal 17H. Also, the main body part 190L of the second heat sink 19L and the terminal 17L are connected via the solder 20L. Consequently, the semiconductor chip 12L is fixed to the second heat sink 19L via the terminal 17L. The main body parts 190H and 190L are disposed to be arranged in the X-direction and are disposed at substantially the same positions in the Z-direction. Also, the respective heat dissipation surfaces 190b of the main body parts 190H and 190L are exposed from the back surface 11b of the sealing resin body 11, while being arranged in the X-direction.

Of the extending parts 191, the upper-arm extending part 191H overlaps the tip portion of the joint part 16 in a projected view along the Z-direction, as shown in FIG. 3. As shown in FIG. 4, the extending part 191H is connected to the joint part 16 via a solder 21. In the Z-direction, the joint part 16 is disposed closer to the semiconductor chip 12 than the extending part 191H. The joint part 16 has a facing surface 16a facing the extending part 191H and a back surface 16b opposite to the facing surface 16a. The solder 21 is interposed between the facing surface 191a of the extending part 191H and the facing surface 16a of the joint part 16. The stacking direction in which the extending part 191H, the solder 21, and the joint part 16 are stacked generally coincides with the Z-direction.

As shown in FIG. 3, the lower-arm extending part 191L overlaps the tip portion of the main terminal 25 in a projected view along the Z-direction. As shown in FIG. 5, the extending part 191L is connected to the joint part 16 via a solder 22. The main terminal 25 is disposed closer to the semiconductor chip 12 than the extending part 191L in the Z-direction. The main terminal 25 has a facing surface 25a facing the extending part 191L and a back surface 25b opposite to the facing surface 25a. The solder 22 is interposed between the facing surface 191a of the extending part 191L and the facing surface 25a of the main terminal 25. Note that the second heat sink 19 (extending part 191) corresponds to a first member. The details of the structure of the second heat sink 19 will be described later.

The main terminal 23 is connected to the higher-potential power source line 5. Accordingly, the main terminal 23 is referred to also as a higher-potential power source terminal or a P-terminal. The main terminal 23 is electrically connected to the first heat sink 14H to extend in the Y-direction and protrude from the side surface 11c of the sealing resin body 11 to the outside. In the present embodiment, the main terminal 23 is provided integrally with the first heat sink 14H by processing the same metal plate.

The main terminal 24 is connected to the output line 7 of the motor 3. Accordingly, the main terminal 24 is referred to also as an output terminal or an O-terminal. The main terminal 24 is electrically connected to the first heat sink 14L to extend in the Y-direction and protrude from the same side surface 11c as that from which the main terminal 23 protrudes to the outside. In the present embodiment, the main terminal 24 is provided integrally with the first heat sink 14L by processing the same metal plate.

The main terminal 25 is connected to the lower-potential power source line 6. Accordingly, the main terminal 25 is referred to also as a lower-potential power source terminal or an N-terminal. As described above, the main terminal 25 is disposed closer to the semiconductor chip 12 than the extending part 191L and connected to the extending part 191L via the solder 22. The main terminal 25 extends in the Y-direction to protrude from the same side surface 11c as that from which the main terminals 23 and 24 protrude to the outside. The respective portions of the main terminals 23, 24, and 25 which protrude from the sealing resin body 11 are disposed at substantially the same positions in the Z-direction. In the X-direction, the main terminal 23, the main terminal 24, and the main terminal 25 are arranged in order of the main terminals 23, 25, and 24. The main terminal 25 corresponds to the second member.

The signal terminals 26 are electrically connected to the pads of the corresponding semiconductor chips 12 via bonding wires 27. In the present embodiment, the aluminum-based bonding wires 27 are used. The signal terminals 26 extend in the Y-direction to protrude from a side surface 11d of the sealing resin body 11 to the outside. Specifically, the signal terminals 26 protrude to the outside from the side surface 11d opposite to the side surface 11c from which the main terminals 23, 24, and 25 protrude.

In the present embodiment, the signal terminals 26 include an upper-arm signal terminal 26H and a lower-arm signal terminal 26L. The signal terminal 26H is connected to the pad of the semiconductor chip 12H, while the signal terminal 26L is connected to the pad of the semiconductor chip 12L.

In the semiconductor device 10 configured as described above, the first heat sinks 14H and 14L, the joint part 16, the main terminals 23, 24, and 25, and the signal terminals 26 are formed of the same metal plate. That is, the lead frame has the first heat sinks 14H and 14L, the joint part 16, the main terminals 23, 24, and 25, and the signal terminals 26.

The sealing resin body 11 integrally seals the semiconductor chips 12, respective portions of the first heat sinks 14, the joint part 16, the terminals 17, respective portions of the second heat sinks 19, respective portions of the main terminals 23, 24, and 25, and respective portions of the signal terminals 26. In the semiconductor device 10, the sealing resin body 11 seals the two semiconductor chips 12H and 12L forming the upper and lower arms corresponding to one phase. Accordingly, the semiconductor device 10 is referred to also as a 2-in-1 package.

As will be described later, the first heat sink 14 and the second heat sink 19 have been subjected to cutting together with the sealing resin body 11. The respective heat dissipation surfaces 14b of the first heat sinks 14H and 14L are located in the same plane and generally flush with the one surface 11a of the sealing resin body 11. Likewise, the respective heat dissipation surfaces 190b of the second heat sinks 19H and 19L (main body parts 190H and 190L) are located in the same plane and generally flush with the back surface 11b of the sealing resin body 11. Thus, the semiconductor device 10 has a double-side heat dissipation structure in which both of the heat dissipation surfaces 14b and 190b are exposed from the sealing resin body 11.

Note that the semiconductor device 10 has through holes 28, 29, and 30. The through hole 28 is formed in the main terminal 23 so as to align the lead frame described above. The through hole 28 is formed in the portion of the main terminal 23 which is uncovered with the sealing resin body 11. The through holes 29 are formed in the vicinity of coupling parts between the first heat sinks 14H and 14L and the main terminals 23 and 24 so as to restrict the peeling of the sealing resin body 11. The through holes 29 are filled with the sealing resin body 11. The through holes 30 are formed in the signal terminals 26 so as to restrict the peeling of the sealing resin body 11. The through holes 30 are filled with the sealing resin body 11.

Next, a description will be given of the details of the structure of each of the second heat sinks 19 and the connection structure thereof on the basis of FIGS. 4 to 8. Although each of FIGS. 6 and 7 is a plan view, the uneven oxide film 191f is hatched for the sake of clarity of illustration.

As shown in FIGS. 4 to 6, the main body part 190 of the second heat sink 19 has a connection region 192 for the solder 20 in the facing surface 190a. In the facing surface 190a of the main body part 190, a groove part 193 is formed so as to surround the connection region 192. The connection region 192 is the region to be connected to the solder 20, i.e., the region to which the solder 20 is applied. The groove part 193 is formed so as to contain the solder 20 that has overflown from the connection region 192. In the present embodiment, the groove part 193 is formed in a loop shape so as to surround the connection region 192. However, the groove part 193 is not limited to the loop shape. For example, it is also possible to use the groove part 193 formed discontinuously so as to surround the connection region 192. The depth and width of the groove part 193 are set appropriately so as to allow the excess solder 20 to be absorbed.

The extending part 191 has a connection region 194 for the corresponding solders 21 and 22 in the facing surface 191a. The connection region 194 has a same shape for both of the solders 21 and 22. In the facing surface 191a of the extending part 191, a groove part 195 is formed so as to surround the connection region 194. The connection region 194 is the region to be connected to the solder 21, 22. The groove part 195 is formed so as to contain the solder 21, 22 that has overflown from the connection region 194. In the present embodiment, the groove part 195 is formed in a loop shape so as to surround the connection region 194. However, the groove part 195 is not limited to the loop shape. For example, it is also possible to use the groove part 195 formed discontinuously so as to surround the connection region 194. The depth and width of the groove part 195 is set appropriately so as to allow the excess solder 21, 22 to be absorbed.

As shown in FIG. 7, on the back surface 191b of the extending part 191, a protruding part 196 is formed to correspond to the groove part 195. The protruding part 196 functions as a positional reference part for the solders 21 and 22 when the solders 21 and 22 are inspected through the back surface 11b of the sealing region body 11 using a supersonic flaw detector (SAT: Scanning Acoustic Tomograph). The protruding part 196 substantially coincides with the groove part 195 in a projected view along the Z-direction. The protruding part 196 is formed in a loop shape so as to surround a back surface part 194a of the connection region 194 in the back surface 191b. The back-surface portion 194a is the portion of the back surface 191b which coincides with the connection region 194 in a projected view along the Z-direction. In the present embodiment, by pressing the metal plate from the facing surface 191a side, the groove part 195 and the protruding part 196 are formed. Note that, from the heat dissipation surface 190b of the main body part 190, the projecting part corresponding to the groove part 193 has been removed by cutting described later.

Figure 8:
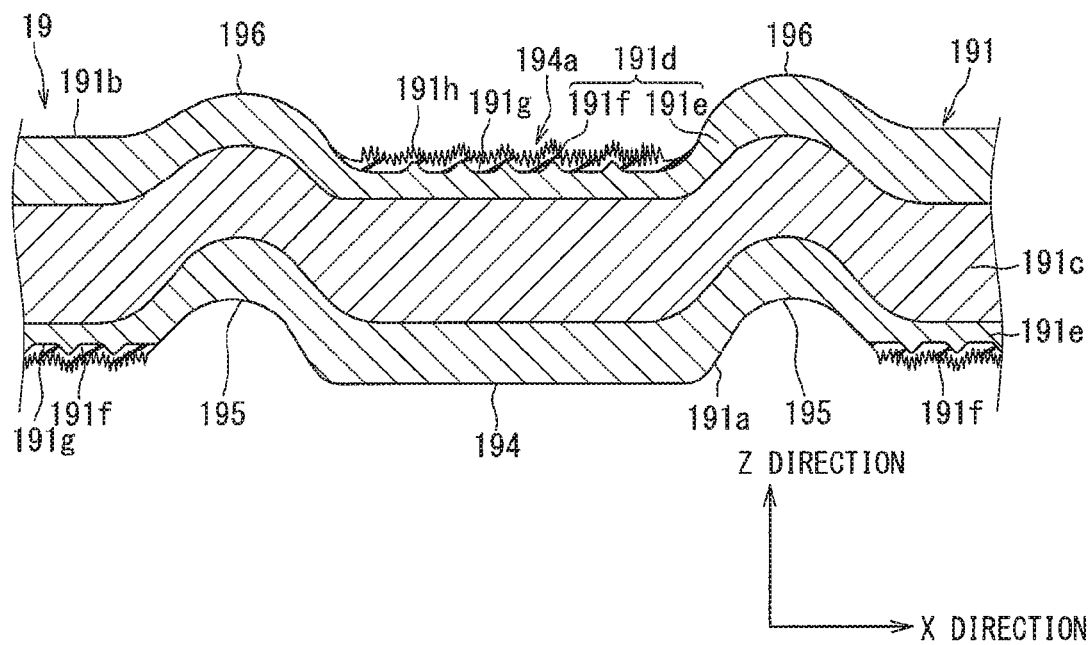
FIG. 8 is a cross-sectional view along the line VIII-VIII in FIG. 7.

As shown in FIG. 8, the extending part 191 of the second heat sink 19 has a base material 191c formed using a metal material and a coated film 191d formed at least on the surface of the base material 191c which is adjacent to the back surface 191b. In the present embodiment, as the material of the base material 191c, Cu is used. Note that, not only the extending part 191, but also the main body part 190 has the base material 191c.

The coated film 191d includes a metal thin film 191e and an uneven oxide film 191f. The metal thin film 191e contains a metal as a constituent material. The metal thin film 191e is formed on a surface of the base material 191c. That is, the metal thin film 191e is formed at least on the surface of the base material 191c which is adjacent to the back surface 191b. In the present embodiment, the metal thin film 191e is formed also on the surface of the base material 191c which is adjacent to the facing surface 191a. The metal thin films 191e are formed on the surfaces of the second heat sink 19 except for the heat dissipation surface 190b. From the heat dissipation surface 190b, the metal thin film 191e has been removed by cutting.

The metal thin film 191e is formed by, e.g., plating or vapor deposition. For the metal thin film 191e, a configuration including a film containing Ni as a main component is preferable. More preferably, a configuration including an electroless Ni plating film is used. The electroless Ni plating film contains P (phosphorus) in addition to Ni as the main component.

In the present embodiment, of the metal thin film 191e adjacent to the facing surface 191a, the portion where the uneven oxide film 191f is not formed has the electroless Ni plating film and an Au plating film formed over the electroless Ni plating film. On the other hand, of the metal thin film 191e adjacent to the facing surface 191a, the portion where the uneven oxide film 191f is formed has the electroless Ni plating film. Thus, the Au plating film is not present on the region of the facing surface 191a where the uneven oxide film 191f is formed because the Au plating film is removed by laser beam irradiation described later and the uneven oxide film 191f is formed from the lower-layer electroless Ni plating film. The metal thin film 191e adjacent to a surface other than the facing surface 191a, e.g., adjacent to the back surface 191b does not have the electroless Ni plating film.

Note that the main body portion 190 also has the same configuration. Specifically, of the metal thin film 191e adjacent to the facing surface 190a, the portion where the uneven oxide film 191f is not formed includes the electroless Ni plating film and the Au plating film formed over the electroless Ni plating film. On the other hand, of the metal thin film 191e adjacent to the facing surface 190a, the portion where the uneven oxide film 191f is formed has the electroless Ni plating film.

As long as conditions for the laser beam irradiation described later are the same, the uneven oxide film 191f formed from the electroless Ni plating film is thicker than the uneven oxide film 191f formed from an electroplated Ni film. The melting point of the electroless Ni plating film (Ni—P) is about 800 degrees (° C.), though the melting point varies depending on the content of P. On the other hand, the melting point of the electroplated Ni film (Ni) is about 1450 degrees (° C.). It can be considered that, since the electroless Ni plating film thus has the lower melting point, the electroless Ni plating film is melted and evaporated with a lower-energy laser beam, and consequently the uneven oxide film 191f is thicker.

In the surface of the metal thin film 191e, as shown in FIG. 8, a plurality of depressed parts 191g are locally formed. As will be described later, the depressed parts 191g are formed by irradiation with a pulse oscillation laser beam. For example, each one of the depressed parts 191g is formed for each one pulse. The depressed parts 191g correspond to laser beam spots. In addition, in the direction in which the laser beam is scanned, the adjacent depressed parts 191g are consecutive. Each of the depressed parts 191g has a width of 5 µm to 300 µm. The depth of the depressed part 191g is 0.5 µm to 5 µm.

When the depth of the depressed part 191g is smaller than 0.5 µm, the melting and vapor deposition of the surface of the metal thin film 191e caused by the laser beam irradiation is insufficient so that the uneven oxide film 191f described later is less likely to be formed. When the depth of the depressed part 191g is larger than 0.5 µm, the surface of the metal thin film 191e is more likely to be melted and scattered. Consequently, in surface formation, melting and scattering is dominant over vapor deposition, and the uneven oxide film 191f is less likely to be formed.

Over the depressed parts 191g in the surface of the metal thin film 191e, the uneven oxide film 191f is formed. As described above, the depressed parts 191g are a mark left by the laser beam irradiation. The portion of the metal thin film 191e where the uneven oxide film 191f is formed has an average thickness smaller than the average thickness of the portion thereof where the uneven oxide film 191f is not formed. Thus, the smaller average thickness of the portion of the metal thin film 191e where the uneven oxide film 191f is formed is also a mark left by the laser beam irradiation.

The uneven oxide film 191f is made of an oxide of the same metal as forming the metal thin film 191e as a main component. The uneven oxide film 191f has a surface with consecutive depressions and projections. The uneven oxide film 191f is formed on the metal thin film 191e. The uneven oxide film 191f is formed by irradiating the metal thin film 191e with a pulse oscillation laser beam and oxidizing the metal forming the metal thin film 191e. In other words, the uneven oxide film 191f is a film of an oxide formed in the surface of the metal thin film 191e by oxidizing the surface layer of the metal thin film 191e. Accordingly, it can also be said that a portion of the metal thin film 191e provides the uneven oxide film 191f. In the present embodiment, $Ni_2O_3$ accounts for 80% of the components forming the uneven oxide film 191f, NiO accounts for 10% thereof, and Ni accounts for 10% thereof. Thus, the main component of the uneven oxide film 191f is the oxide of Ni contained in the metal thin film 191e.

The uneven oxide film 191f is formed over the surfaces of the depressed parts 191g of the surface of the metal thin film 191e. The average thickness of the uneven oxide film 191f is ten to several hundreds of nanometers. The uneven oxide film 191f is formed conformally along the depressions and projections of the surface of the metal thin film 191e having the depressed parts 191g. The depressions and projections are formed with a pitch finer than the width of each of the depressed parts 191g. That is, the extremely minute depressions and projections are formed. In other words, a plurality of projecting parts 191h (columnar bodies) are formed with a fine pitch. For example, the average width of the projecting parts 191*h* is 1 nm to 300 nm, and the average interval between the projecting parts 191*h* is 1 nm to 300 nm.

The uneven oxide film 191*f* is formed over the entire region of the back surface portion 194*a* of the connection region 194, which is included in the back surface 191*b* of the extending part 191. In other words, the uneven oxide film 191*f* is formed over the entire region of the portion of the back surface 191*b* which is surrounded by the protruding part 196. In the portion of the back surface 191*b* where the uneven oxide film 191*f* is formed, the uneven oxide film 191*f* is a portion of the back surface 191*b*. In the present embodiment, the uneven oxide film 191*f* is formed also over the entire region of the portion of the facing surface 191*a* which is other than the connection region 194 and the groove part 195, i.e., over the entire region of the portion of the facing surface 191*a* which is located externally of the groove part 195.

The uneven oxide film 191*f* is formed also over the entire region of the portion of the facing surface 190*a* of the main body part 190 which is other than the connection region 192 and the groove part 193, i.e., the portion of the facing surface 190*a* which is located externally of the groove part 193. Thus, the uneven oxide film 191*f* is formed over the entire regions of the portions of the facing surfaces 190*a* and 191*a* of the second heat sink 19 which are other than the connection regions 192 and 194 and the groove parts 193 and 195. In addition, the uneven oxide films 191*f* are formed also on the side surfaces of the terminal 17 as the surfaces of the terminal 17 other than the junction surfaces with the solders 18 and 20. As described above, the terminal 17 also includes the base material formed using Cu and the metal thin film containing Ni as the main component and formed on the surface of the base material. By irradiating the metal thin film with a pulse oscillation laser beam, the uneven oxide films 191*f* are formed.

In the present embodiment, the uneven oxide film 191*f* is formed over the portion of the facing surface 191*a* of the extending part 191 of the second heat sink 19 which is other than the connection region 194 for the solder 21, 22 and the groove part 195. Compared to a configuration which does not have the uneven oxide film 191*f*, i.e., in which the surface of the metal thin film 191*e* is exposed, the configuration having the uneven oxide film 191*f* can reduce wettability to the solder 21, 22.

Also, as a result of having the uneven oxide film 191*f*, the facing surface 191*a* is formed with the minute depressions and projections. Into such a roughened surface, the solders 21 and 22 are unlikely to gain entry. Consequently, the contact areas between respective portions of the solders 21 and 22 and the facing surface 191*a* are reduced, and respective portions of the solders 21 and 22 are formed into spherical shapes under surface tension. That is, contact angles are increased. As a result, at the portion where the uneven oxide film 191*f* is formed, the wettability to the solders 21 and 22 can be reduced. Thus, it is possible to restrict the solders 21 and 22 from wet-spreading to the outside of the groove part 195. Likewise, using the uneven oxide film 191*f* formed on the facing surface 190*a*, it is possible to restrict the solder 20 form wet-spreading to the outside of the groove part 193.

Likewise, using the uneven oxide films 191*f* formed on the side surfaces of the terminal 17, it is also possible to restrict the solder 20 from wet-spreading over the side surfaces and flowing into the solder 18 adjacent to the semiconductor chip 12.

Also, as a result of having the uneven oxide film 191*f*, the facing surfaces 190*a* and 191*a* have increased contact areas with the sealing resin body 11. In addition, the sealing resin body 11 clings to the depressions and projections of the uneven oxide film 191*f* to cause an anchoring effect. Consequently, it is possible to improve the adhesion between each of the facing surfaces 190*a* and 191*a* and the sealing resin body 11 and form solid connection structures between the facing surfaces 190*a* and 191*a* and the sealing resin body 11. Particularly when the metal thin film 191*e* containing Ni is formed, it is possible to maintain the connection structures which are stable over a long period of time.

Next, a description will be given of a method of manufacturing the semiconductor device 10 (electronic device) described above on the basis of FIGS. 9 to 12.

First, the individual components of the semiconductor device 10 are prepared. That is, each of the semiconductor chips 12, the first heat sinks 14 including the joint part 16, the terminals 17, the second heat sinks 19, the main terminals 23, 24, and 25, and the signal terminals 26 is prepared. In the preparation step, the second heat sinks 19 each having the metal thin film 191*e* formed at least on the surface of the base material 191*c* which is adjacent to the back surface 191*b* are prepared.

In the present embodiment, the second heat sinks 19 are prepared in each of which the electroless Ni plating film is formed as the metal thin film 191*e* over the entire back surface 191*b*, while the electroless Ni plating film and the Au plating film over the electroless Ni plating film are formed as the metal thin film 191*e* over the entire facing surfaces 190*a* and 191*a*. At this time, the thickness of the electroless Ni film is set to about 10 μm. Also, the terminals 17 are prepared. As each of the terminals 17 also, a terminal in which an electroless Ni plating film is formed as a metal thin film on the surface of a base material is prepared. For the first heat sinks 14, the main terminals 23, 24, and 25, and the signal terminals 26, a lead frame including the first heat sinks 14, the main terminals 23, 24, and 25, and the signal terminals 26 is prepared.

Next, the uneven oxide film 191*f* is formed by laser beam irradiation. By irradiating the surface of the metal thin film 191*e* which is adjacent to the back surface 191*b* of the extending part 191 of each of the second heat sinks 19 with a pulse oscillation laser beam, the surface of the metal thin film 191*e* is melted and evaporated. Specifically, by the laser beam irradiation, the surface portion of the metal thin film 191*e* is melted and evaporated (vaporized) to float in ambient air.

A pulse oscillation laser beam is adjusted such that the energy density thereof is more than 0 J/cm$^2$ and not more than 100 J/cm$^2$, and the pulse width thereof is not more than 1 microsecond. To satisfy the conditions, a YAG laser, a YVO$_4$ laser, a fiber laser, or the like can be used. For example, in the case of using the YAG laser, it is sufficient for the energy density to be not less than 1 J/cm$^2$. In the case of using electroless Ni plating, the metal thin film 191*e* can be processed even when the energy density is about 5 J/cm$^2$. Note that the energy density is referred to also as pulse fluence.

Figure 9:
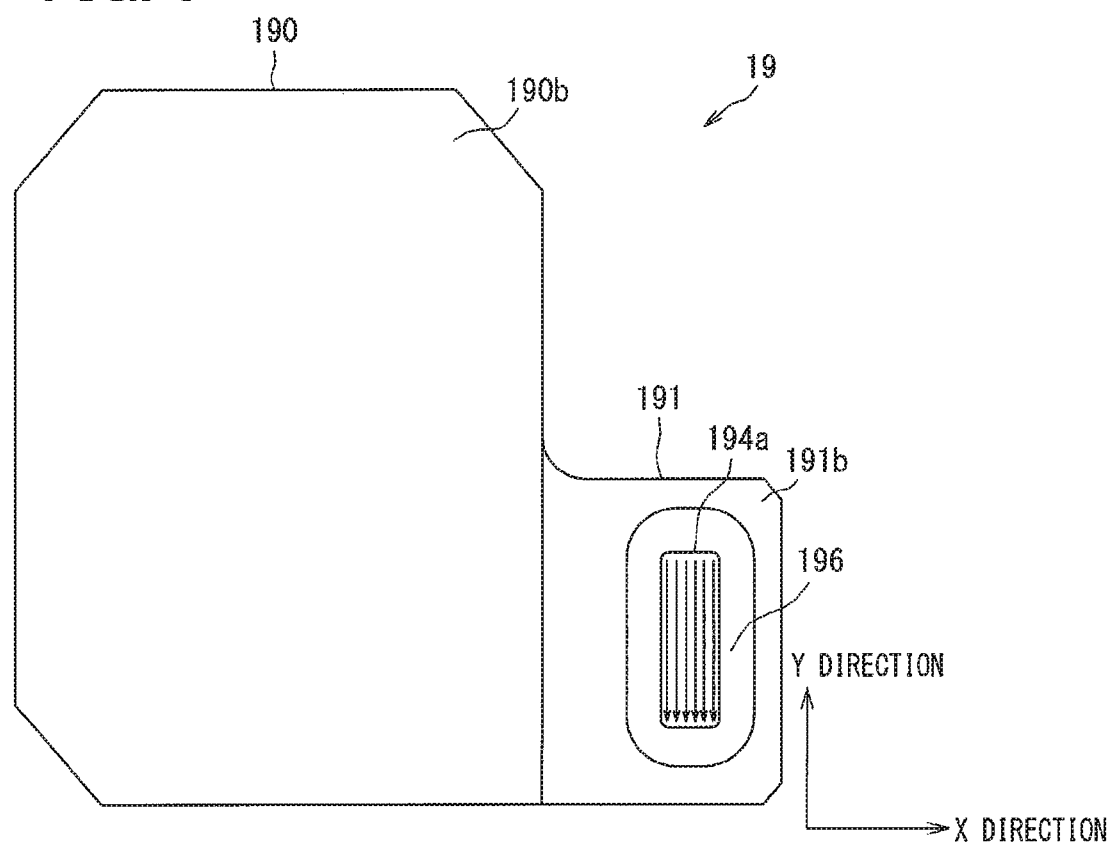
FIG. 9 is a plan view showing a method of manufacturing the semiconductor device, which corresponds to FIG. 7.

At this time, by relatively moving the light source of the laser beam and the second heat sink 19, as shown in FIG. 9, the laser beam is successively applied to a plurality of points on the back surface portion 194*a* of the connection region 194 surrounded by the protruding part 196. Note that either the light source of the laser beam or the second heat sink 19 may be moved. It may also be possible to scan the laser beam by the rotating operation of a mirror. That is, it may also be possible to scan the laser beam and thus successively apply the laser beam to the plurality of points on the back surface portion 194a.

For example, as shown in FIG. 9, when the laser beam is scanned in the Y-direction and the irradiation of the back surface portion 194a from one end to the other end is completed, the region to be irradiated with the laser beam is shifted in the X-direction. That is, the laser beam is scanned in the X-direction. Then, the laser beam is similarly scanned in the Y-direction to irradiate the back surface portion 194a from one end to the other. By repeating this, substantially the entire region of the back surface portion 194a is irradiated with the laser beam. That is, the laser beam is applied to lattice points with a predetermined pitch in XY-coordinates.

In the present embodiment, the laser beam is scanned in the Y-direction such that adjacent laser beam spots (irradiation range corresponding to one pulse) partially overlap in the Y-direction. Also, the laser beam is scanned in the X-direction such that the adjacent laser beam spots partially overlap in the X-direction. By thus applying the laser beam and melting and evaporating the surface of the metal thin film 191e, the depressed parts 191g are formed in the surface of the metal thin film 191e. The portion of the metal thin film 191e which is irradiated with the laser beam has an average thickness smaller than the average thickness of the portion of the metal thin film 191e which is not irradiated with the laser beam. The plurality of depressed parts 191g formed to correspond to the laser beam spots are consecutive in the X-direction and also consecutive in the Y-direction. As a result, the depressed parts 191g as a mark left by the laser irradiation have a scaly pattern.

Next, the melted portion of the metal thin film 191e is solidified. Specifically, the melted and evaporated metal thin film 191e is vapor-deposited on the portion irradiated with the laser beam and the peripheral portion thereof. By thus vapor-depositing the melted and evaporated metal thin film 191e, the uneven oxide film 191f is formed on the surface of the metal thin film 191e. The uneven oxide film 191f is formed mainly on the portion of the metal thin film 191e which is irradiated with the laser beam.

Thus, on the back surface portion 194a of the connection region 194 of the extending part 191, the uneven oxide film 191f is formed. In the laser beam irradiation, when the energy density was set to 150 J/cm$^2$ or 300 J/cm$^2$ higher than 100 J/cm$^2$, the uneven oxide film 191f was not formed. When a continuous oscillation laser beam, not the pulse oscillation laser beam, was applied also, the uneven oxide film 191f was not formed.

In the present embodiment, not only on the back surface portion 194a, but also on the facing surfaces 190a and 191a of each of the second heat sinks 19 and the side surfaces of the terminal 17, the uneven oxide films 191f are similarly formed. For example, in the case of forming the uneven oxide films 191f on the facing surfaces 190a and 191a, the pulse oscillation laser beam is applied to melt and evaporate the surface layer portion of the lower-layer electroless Ni plating film, while removing the upper-layer Au plating film, and form the uneven oxide films 191f on the surfaces of the metal thin films 191e. On the terminal 17, the uneven oxide film 191f is formed in the same manner as formed on the back surface portion 194a.

Next, the semiconductor chips 12 and the first heat sinks 14 are connected via the solders 15 to form connection bodies 31. In the present embodiment, as the connection bodies 31, an upper-arm connection body 31H and a lower-arm connection body 31L are formed.

Figure 10:
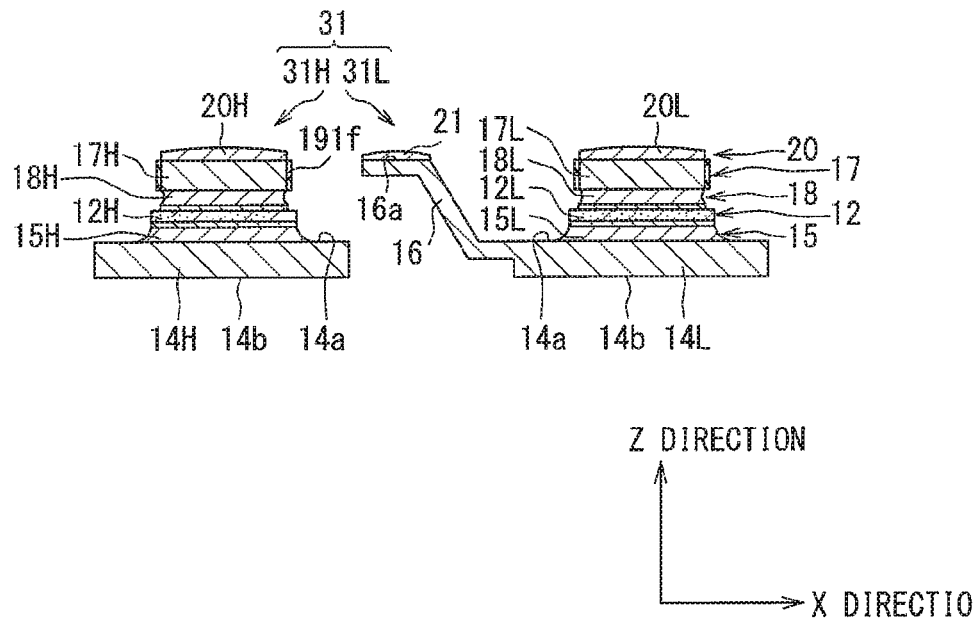
FIG. 10 is a cross-sectional view showing the method of manufacturing the semiconductor device, which corresponds to FIG. 4.

A description will be given first of a method of forming the connection body 31H. As shown in FIG. 10, on the facing surface 14a of the first heat sink 14H, the semiconductor chip 12H is placed via the solder 15H. Next, the terminal 17H having the solder 18H and the solder 20H which are placed in advance as pre-solders on the both surfaces thereof is placed on the semiconductor chip 12H such that the solder 18H is adjacent to the semiconductor chip 12H. The solder 20H is placed in an amount which allows height variations in the semiconductor device 10 to be absorbed.

Then, in the stacked state, the solders 15H, 18H, and 20H are caused to reflow (1st reflow) to connect the semiconductor chip 12H and the first heat sink 14H via the solder 15H. Also, the semiconductor chip 12H and the terminal 17H are connected via the solder 18H. The second heat sink 19H (main body part 190H) to which the solder 20H is to be connected has not been prepared yet so that the solder 20H shows a protruding shape having an apex at the center of the facing surface thereof facing the second heat sink 19H under surface tension.

The connection body 31L is also formed similarly to the connection body 31H. The formation of the connection body 31L is different from that of the connection body 31H in that, before being caused to reflow, the solder 21 is placed on the facing surface 16a of the joint part 16 facing the extension part 191H. Similarly to the solder 20H, the solder 21 is placed in an amount which allows height variations in the semiconductor device 10 to be absorbed.

Then, in the stacked state, the solders 15L, 18L, 20L, and 21 are caused to reflow (1st reflow) to connect the semiconductor chip 12L and the first heat sink 14L via the solder 15L. Also, the semiconductor chip 12L and the terminal 17L are connected via the solder 18L. The second heat sink 19L (main body part 190L) to which the solder 20L is to be connected has not been prepared yet so that the solder 20L shows a protruding shape having an apex at the center of the facing surface thereof which is to face the second heat sink 19L under surface tension. Also, the extending part 191H of the second heat sink 19H to which the solder 21 is to be connected has not been prepared yet so that the solder 21 shows a protruding shape under surface tension.

Then, the pads of the semiconductor chips 12H and 12L corresponding to the signal terminals 26H and 26L are connected thereto with the bonding wires 27.

Then, the connection bodies 31 and the corresponding second heat sinks 19 are connected via the solders 20. In the present embodiment, the connection body 31H and the second heat sink 19H are connected via the solder 20H, while the connection body 31L and the second heat sink 19L are connected via the solder 20L. Also, the upper arm and the lower arm are connected via the solder 21. Also, the main terminal 25 and the extending part 191L are connected via the solder 22. That is, the solders 20, 21, and 22 are caused to simultaneously reflow (2nd reflow).

Figure 11:
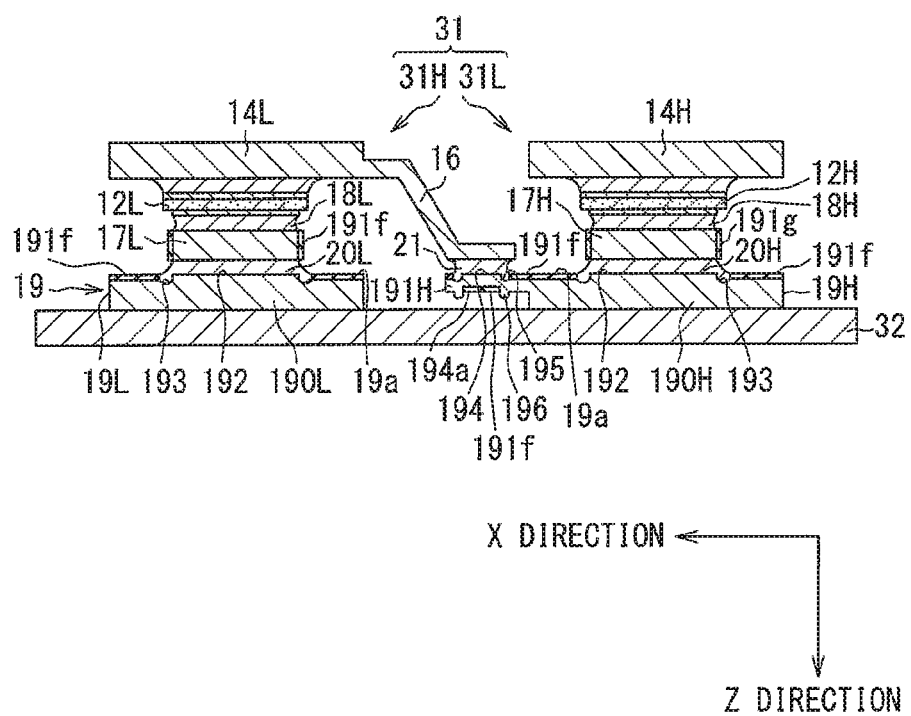
FIG. 11 is a cross-sectional view showing the method of manufacturing the semiconductor device, which corresponds to FIG. 4.

As shown in FIG. 11, the second heat sinks 19H and 19L are placed over a seat 32 such that the facing surfaces 19a face upward. At this time, on the facing surface 191a of the extending part 191L of the second heat sink 19L, the solder 22 (e.g., solder foil) is placed, though not illustrated. The solder 22 is placed in an amount which allows height variations in the semiconductor device 10 to be absorbed. Note that the solder 22 may also be placed in advance as a pre-solder on the main terminal 25.

Next, the connection bodies 31H and 31L are placed on the respective facing surfaces 19a of the second heat sinks 19H and 19L such that the terminals 17H and 17L face the corresponding second heat sinks 19H and 19L. The solder 21 is interposed between the joint part 16 and the extending part 191H. On the other hand, the solder 22 is interposed between the extension part 191L and the main terminal 25.

Then, with the second heat sinks 19H and 19L facing downward, the 2nd reflow is performed. In the 2nd reflow, a load is applied to the first heat sinks 14H and 14L to allow the semiconductor device 10 to have a predetermined height. Specifically, a spacer not shown is disposed between the main body parts 190H and 190L of the second heat sinks 19H and 19L and the seat 32 and brought into contact with both of the main body parts 190H and 190L and the seat 32. Thus, the semiconductor device 10 is allowed to have the predetermined height. That is, the seat 32 and the spacer function as a height adjustment member.

As described above, to control height variations, the solders 20H and 20L are placed in rather large amounts between the terminals 17H and 17L and the main body parts 190H and 190L of the second heat sinks 19H and 19L. Consequently, in the 2nd reflow, there is no shortage of the solders 20H and 20L between the terminals 17H and 17L and the second heat sinks 19H and 19L to allow reliable connection to be provided therebetween. Since the solder 21 is placed in a rather large amount between the extending part 191H and the joint part 16, in the 2nd reflow, there is no shortage of the solder 21 between the extending part 191H and the joint part 16 to allow reliable connection to be provided therebetween. Since the solder 22 is placed in a rather large amount between the extending part 191L and the main terminal 25, in the 2nd reflow, there is no shortage of the solder 22 between the extending part 191L and the main terminal 25 to allow reliable connection to be provided therebetween.

Even when the excess solders 20H and 20L are pushed out of the spaces between the terminals 17H and 17L and the second heat sinks 19H and 19L as a result of the application of the load describe above or the like, the excess solders 20H and 20L are contained in the groove part 193. Around the groove part 193, the uneven oxide film 191f is formed to restrict the solders 20H and 20L from wet-spreading to the outside of the groove part 193. In addition, over the side surfaces of the terminals 17H and 17L also, the uneven oxide films 191f are formed to restrict the solders 20H and 20L from wet-spreading to the side surfaces of the terminals 17H and 17L.

Likewise, even when the excess solder 21 is pushed out of the space between the extending part 191 and the joint part 16, the excess solder 21 is contained in the groove part 195. Around the groove part 195, the uneven oxide film 191f is formed to restrict the solder 21 from wet-spreading to the outside of the groove part 195. Likewise, even when the excess solder 22 is pushed out of the space between the extending part 191L and the main terminal 25, the excess solder 22 is contained in the groove part 195. Around the groove part 195, the uneven oxide film 191f is formed to restrict the solder 22 from wet-spreading to the outside of the groove part 195.

Note that each of the first reflow and the second reflow is assumed to be a reflow performed in a hydrogen atmosphere. Accordingly, a natural oxide film on the metal surface which is unneeded for soldering can be removed by reduction. This allows a fluxless solder to be used as each of the solders 15, 18, 20, 21, and 22. In addition, it is possible to restrict voids from being formed in the solders 15, 18, 20, 21, and 22 by pressure reduction. Note that, since the thickness of the uneven oxide film 191f is also reduced by reduction, the uneven oxide film 191f having an intended thickness is formed by laser beam irradiation such that the uneven oxide film 191f remains even when reduced. As described above, the metal thin film 191e preferably includes the electroless Ni plating film since the uneven oxide film 191f can be thickened thereby.

Note that, when the uneven oxide film 191f is formed only on the back surface 191b of the extending part 191 of the second heat sink 19, the uneven oxide film 191f can be formed after the connection bodies 31 are formed or after the 2nd reflow is performed. That is, the uneven oxide film 191f can also be formed before the sealing resin body 11 is molded.

Then, by a transfer mold method, the sealing resin body 11 is molded. In the present embodiment, the sealing resin body 11 is molded so as to completely cover the first heat sinks 14 and the second heat sinks 19. In this case, the molded sealing resin body 11 is cut together with respective portions of the first heat sinks 14 and the second heat sinks 19 to expose the heat dissipation surfaces 14b and 190b of the first heat sink 14 and the second heat sink 19. Accordingly, the heat dissipation surfaces 14b and 190b are cut surfaces. In addition, the one surface 11a and the back surface 11b of the sealing resin body 11 are also cut surfaces. Also, the heat dissipation surface 14b is generally flush with the one surface 11a, while the heat dissipation surfaces 190b are generally flush with the back surface 11b.

Note that the sealing resin body 11 may also be molded in the state where the heat dissipation surfaces 14b and 190b of the first heat sinks 14 and the second heat sinks 19 are pressed against the cavity wall surface of a mold die in close contact relation thereto. In this case, at the time when the sealing resin body 11 is molded, the heat dissipation surfaces 14b and 190b are exposed from the sealing resin body 11. This eliminates the need for cutting after molding.

Figure 12:
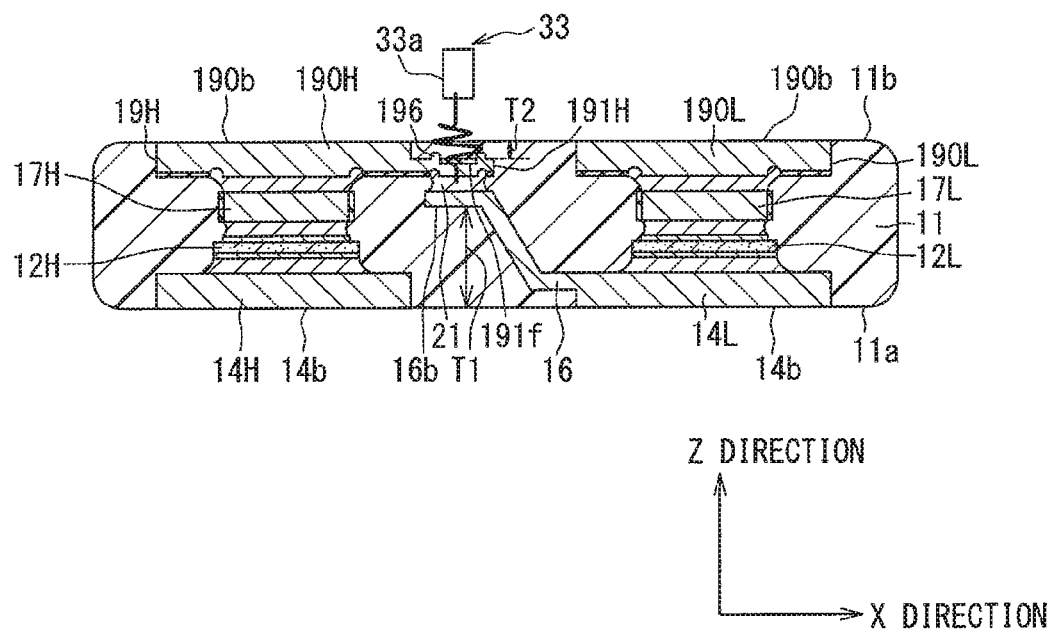
FIG. 12 is a cross-sectional view showing the method of manufacturing the semiconductor device, which corresponds to FIG. 4.

After the sealing resin body 11 is molded, as shown in FIG. 12, using a supersonic flaw detector 33, the solder 21 is inspected through the extending part 191a of the second heat sink 19 in the Z-direction. Specifically, from a probe (probing needle) 33a of the supersonic flaw detector 33, a supersonic wave is transmitted toward the extending part 191 and the reflected wave thereof is detected using the probe 33a. At this time, the protruding part 196 is used as a positional reference part. Using the transmitted/received supersonic waves, the position of the protruding part 196 is detected to allow the back surface portion 194a, i.e., the solder 21 to be specified with high positional accuracy. Then, from the result of transmitting/receiving the supersonic wave, a defect such as a void in the solder 21 is detected.

In the present embodiment, as shown in FIG. 12, in the Z-direction, a thickness T2 of the portion of the sealing resin body 11 which covers the back surface 191b of the extending part 191 is smaller than a thickness T1 of the portion of the sealing resin body 11 which covers the back surface 16b of the joint part 16. The joint part 16 and the extending part 191 have substantially the same thicknesses. Accordingly, an inspection on the solder 21 is performed through the thinner portion of the sealing resin body 11. An inspection on the solder 22 is similarly performed. Note that an inspection may also be performed on the solders other than the solders 21 and 22.

Then, by removing the unneeded portion of the lead frame, the semiconductor device 10 can be obtained. Note that the inspections on the solders 21 and 22 using the supersonic flaw detector 33 can also be performed after the unneeded portion of the lead frame is removed.

Next, a description will be given of the effects of the semiconductor devices 10 and the manufacturing method thereof each described above.

In the present embodiment, the uneven oxide film 191*f* is formed on the back surface portion 194*a* of the connection region 194 of the extending part 191 of each of the second heat sinks 19. The uneven oxide film 191*f* has the surface with the minute depressions and projections. This increases the contact area between the back surface portion 194*a* and the sealing resin body 11. In addition, the sealing resin body 11 clings to the depressions and projections of the uneven oxide film 191*f* to cause the anchoring effect. This can improve the adhesion between the back surface portion 194*a* of the extending part 191 and the sealing resin body 11 and restrict the sealing resin body 11 from peeling from the back surface portion 194*a*. Even when, e.g., vibration resulting from cutting when the heat dissipation surface 190*b* is exposed is transmitted to the extending part 191, it is possible to restrict the sealing resin body 11 from peeling from the back surface portion 194*a*. Consequently, it is possible to accurately inspect the solders 21 and 22 from the extending part 191 side using the supersonic flaw detector 33.

In addition, by performing the irradiation with the pulse oscillation laser beam, the uneven oxide film 191*f* is formed on the metal thin film 191*e*. Since the metal thin film 191*e* and the base material 191*c* are protected with the uneven oxide film 191*f*, the corrosion of the back surface portion 194*a* of the extending part 191 can more reliably be suppressed than in a configuration in which the metal thin film 191*e* is not protected with the uneven oxide film 191*f* and is exposed. For example, using the uneven oxide film 191*f*, the metal thin film 191*e* and the base material 191*c* can be protected from a chloride-based compound remaining in the sealing resin body 11. Also, the metal thin film 191*e* and the base material 191*c* can be protected from the moisture that has entered from the outside through the interface between the sealing resin body 11 and the second heat sink 19 or the like. Therefore, it is possible to restrict the peeling of the sealing resin body 11 resulting from the corrosion of the back surface portion 194*a* and consequently allows the solders 21 and 22 to be accurately inspected using the supersonic flaw detector 33.

In particular, in the present embodiment, the thickness of the portion of the sealing resin body 11 which covers the back surface 191*b* of the extending part 191 is smaller than the thickness of the portion of the sealing resin body 11 which covers the back surface 16*b* of the joint part 16. Also, the thickness of the portion of the sealing resin body 11 which covers the back surface 191*b* of the extending part 191 is smaller than the thickness of the portion of the sealing resin body 11 which covers the back surface 25*b* of the main terminal 25. Consequently, it is possible to more reliably restrict the attenuation of the supersonic wave in the sealing resin body 11 than in the configuration in which the uneven oxide film 191*f* is provided on the side where the sealing resin body 11 is thicker, e.g., on the back surface 16*b* of the joint part 16, and an inspection is performed on the solder 21 from the joint part 16 side. That is, the solders 21 and 22 can be inspected with high accuracy.

In the state where the solders 21 and 22 are not contained in the groove part 195, the interface between the sealing resin body 11 (resin) and the extending part 191 (metal) is formed in the groove part 195. Consequently, it is easy to detect the position of the groove part 195 using the supersonic flaw detector 33. However, when the solders 21 and 22 overflow from the connection region 194 and are contained in the groove part 195, the interfaces between the solders 21 and 22 (metal) and the extending part 191 (metal) are formed in the groove part 195. In this case, there is no large acoustic impedance difference so that it is difficult to detect the position of the groove part 195 using the supersonic flaw detector 33.

By contrast, in the present embodiment, in the facing surface 191*a* of the extending part 191, the groove part 195 is formed to surround the connection region 194 while, on the back surface 191*b* of the extending part 191, the protruding part 196 is formed to surround the back surface portion 194*a* of the connection region 194. Consequently, even in the state where the solders 21 and 22 are contained in the groove part 195, it is possible to detect the protruding part 196. In addition, using the position of the protruding part 196 as a reference, the solders 21 and 22 can be inspected with high positional accuracy. Since the back surface 191*b* is closer to the back surface 11*b* of the sealing resin body 11 than the facing surface 191*a*, it is possible to restrict the attenuation of the supersonic wave and detect the positional reference part with high positional accuracy.

Also, the protruding part 196 is formed simultaneously with the groove part 195 by press working. This allows the positional reference part to be formed with high positional accuracy on the back surface 191*b* side to correspond to the groove part 195. This also allows the manufacturing process to be simplified.

Second Embodiment

For the present embodiment, it is possible to refer to the previous embodiment. Accordingly, a description of the same parts as those of the semiconductor device 10 shown in the previous embodiment and the manufacturing method thereof is omitted.

Figure 13:
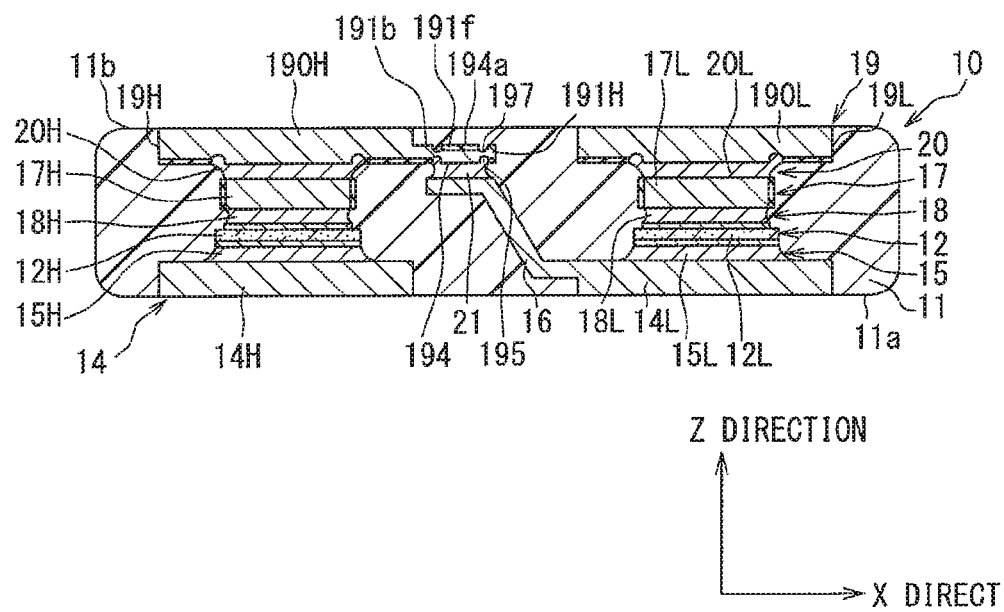
FIG. 13 is a cross-sectional view showing a schematic configuration of a semiconductor device according to a second embodiment, which corresponds to FIG. 4.

In the present embodiment, as shown in FIG. 13, in the back surface 191*b* of the extending part 191, a groove part 197 is formed as the positional reference part. In the present embodiment, the groove part 195 corresponds to a first groove part, while the groove part 197 corresponds to a second groove part. The groove part 197 is formed to correspond to the groove part 195. The groove part 197 is formed to coincide with the groove part 195 in a projected view along the Z-direction. The groove part 197 can be formed by, e.g., etching.

Thus, in the case of using the configuration having the groove part 197 as the positional reference part also, the same effects as achieved in the first embodiment can be achieved.

Third Embodiment

Figure 14:
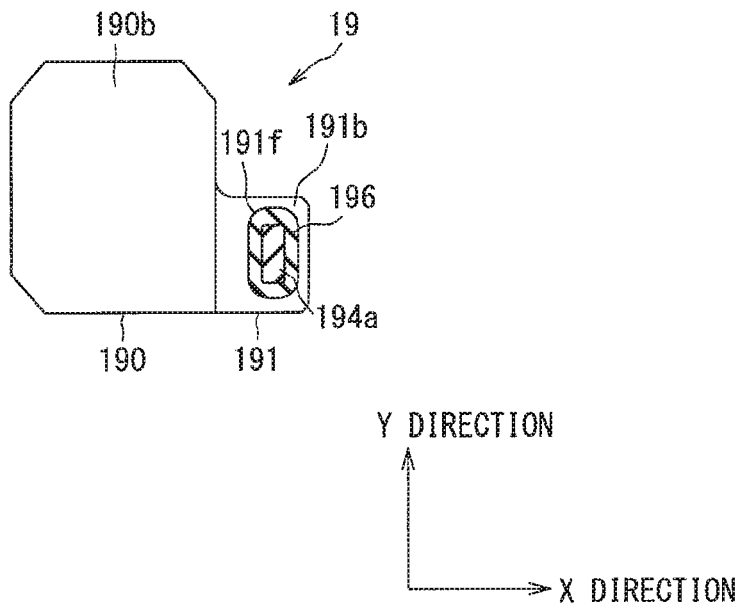
FIG. 14 is a plan view of a semiconductor device according to a third embodiment in which a second heat sink is viewed from a heat dissipation surface side and which corresponds to FIG. 7.

For the present embodiment, it is possible to refer to the previous embodiments. Accordingly, a description of the same parts as those of the semiconductor devices 10 each shown in the previous embodiments and the manufacturing methods thereof is omitted. FIG. 14 is a plan view but, for improved clarity of illustration, the uneven oxide film 191*f* is hatched.

In the present embodiment, as shown in FIG. 14, the uneven oxide film 191*f* is formed also over the protruding part 196 as the positional reference part of the back surface 191*b* of the extending part 191. That is, the uneven oxide film 191*f* is formed over the back surface portion 194*a* of the connection region 194 and the protruding part 196.

This can restrict the sealing resin body 11 from peeling from the protruding part 196. Accordingly, it is possible to more reliably detect the position of the protruding part 196 using the supersonic flaw detector 33. In addition, since the sealing resin body 11 is unlikely to peel from the protruding part 196, it is possible to restrict the peeling of the sealing resin body 11 from extending from around the back surface portion 194a to the back surface portion 194a. That is, it is possible to more effectively restrict the sealing resin body 11 from peeling from the back surface portion 194a.

Note that, even when the uneven oxide film 191f is formed in the groove part 197, the same effects can be achieved.

Fourth Embodiment

Figure 15:
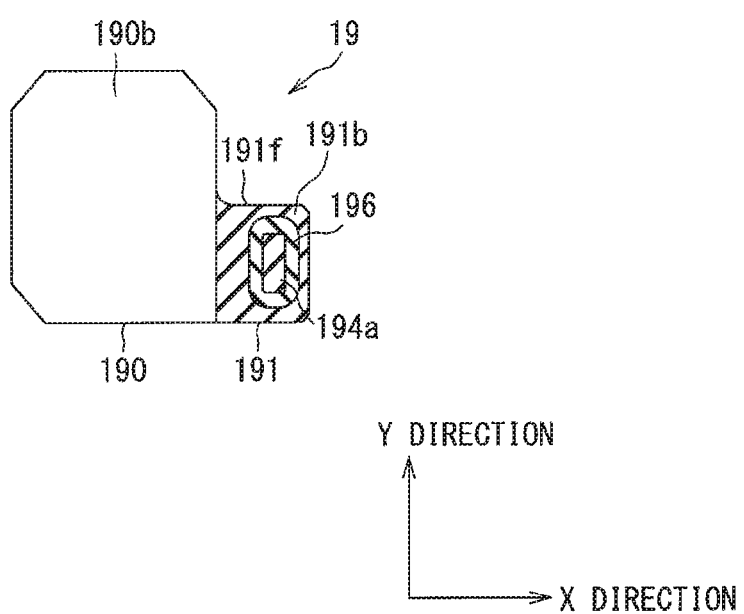
FIG. 15 is a plan view of a semiconductor device according to a fourth embodiment in which a second heat sink is viewed from a heat dissipation surface side and which corresponds to FIG. 7.

For the present embodiment, it is possible to refer to the previous embodiments. Accordingly, a description of the same parts as those of the semiconductor devices 10 shown in the previous embodiments and the manufacturing methods thereof is omitted. FIG. 15 is a plan view but, for improved clarity of illustration, the uneven oxide film 191f is hatched.

In the present embodiment, as shown in FIG. 15, the uneven oxide film 191f is formed on the entire back surface 191b of the extending part 191.

This restricts the peeling of the sealing resin body 11 at the entire back surface 191b. For example, it is possible to restrict the peeling of the sealing resin body 11 from occurring at the edge portion of the back surface 191b of the extending part 191. Accordingly, it is possible to more effectively restrict the sealing resin body 11 from peeling from the back surface portion 194a.

Note that, even when the uneven oxide film 191f is formed in the groove part 197, the same effects can be achieved.

The disclosure of the present description is not limited to the embodiments shown by way of example. The disclosure includes the embodiments shown by way of example and aspects resulting from modifications made by those skilled in the art on the basis thereof. For example, the disclosure is not limited to the combination of elements shown in the embodiments. The disclosure can be implemented using various combinations of elements. The disclosed technical scopes are not limited to the description of the embodiments. Some of the disclosed technical scopes are shown by the description of the claims and are intended be construed to include all modifications and variations within the meaning and scope equivalent to the description of the claims.

In each of the foregoing embodiments, the 2-in-1 package having the two semiconductor chips 12 is shown as an example of the semiconductor device 10. However, the number of the semiconductor chips 12 is not limited. For example, the semiconductor device 10 is also applicable to a 6-in-1 package having the six semiconductor chips 12 forming the upper and lower arms corresponding to three phases.

In the example shown above, the IGBT and the FWD are formed in the same chip. However, the present disclosure is also applicable to a configuration in which the IGBT and the FWD are formed in different chips.

In the example shown above, the semiconductor device 10 has the terminals 17. However, the semiconductor device 10 may also have a configuration which does not have the terminals 17. In this case, it is appropriate to provide the second heat sinks 19 with projecting parts projecting toward the emitter electrodes 13b.

In the example shown above, the heat dissipation surfaces 14b and 19b are exposed from the sealing resin body 11. However, the present disclosure is also applicable to a configuration in which the heat dissipation surfaces 14b and 19b are not exposed from the sealing resin body 11.

In the example shown above, an electronic device is the semiconductor device 10, but the electronic device is not limited thereto. The present disclosure is applicable to any electronic device including an electronic component, a sealing resin body sealing the electronic component, a first member having at least a portion disposed in the sealing resin body, and a second member connected to the first member via a solder in the sealing resin body.

The metal forming the metal thin film 191e is not limited to Ni. Also, the uneven oxide film 191f is not limited to an oxide of Ni. It is sufficient for the constituent material of the uneven oxide film 191f to be an oxide of the same metal as forming the metal thin film 191e.

In the example shown above, the uneven oxide films 191f are formed on the facing surfaces 190a and 191a of the second heat sinks 19 as well as the side surfaces of the terminals 17. However, it is also possible to adopt a configuration which does not have the uneven oxides film 191f on at least either one of the facing surfaces 190a and 191a of the second heat sinks 19 and the side surfaces of the terminals 17.

Note that the uneven oxide film 191f may also be formed only over the protruding part 196 as the positional reference part or in the groove part 197 as the positional reference part on or in the back surface 191b of the extending part 191. This can restrict the sealing resin body 11 from peeling from the protruding part 196. Consequently, it is possible to more reliably detect the position of the protruding part 196 using the supersonic flaw detector 33. In addition, since the sealing resin body 11 is unlikely to peel from the protruding part 196, it is possible to restrict the peeling of the sealing resin body 11 from extending from around the back surface portion 194a to the back surface portion 194a. Also, the region where the uneven oxide film 191f is formed is not limited to the positional reference part. The uneven oxide film 191f may also be formed so as to surround the back surface portion 194a. For example, the uneven oxide film 191f may also be formed only on the edge portion of the back surface 191b.

The invention claimed is:
1. An electronic device, comprising:
an electronic component;
a sealing resin body sealing the electronic component;
a first member having at least a portion located in the sealing resin body; and
a second member connected to the first member via a solder in the sealing resin body, wherein
the first member has a facing surface facing the second member and a back surface opposite to the facing surface, the first member includes a base material formed of a metal material and a coated film provided at least on a surface of the base material which is adjacent to the back surface of the first member,
the coated film includes a metal thin film provided on the surface of the base material and an uneven oxide film provided on the metal thin film and made of an oxide of a metal that is a same metal as a main component of the metal thin film, and
the uneven oxide film is provided in the back surface of the first member so as to overlap at least an entirety of a connection region of the facing surface of the first member which is connected to the solder in a projected view along a stacking direction in which the first member, the solder, and the second member are stacked.

2. The electronic device according to claim 1, wherein the sealing resin body has a thickness in the stacking direction in such a manner that a portion of the sealing resin body which covers the back surface of the first member is thinner than a portion of the sealing resin body which covers a back surface of the second member opposite to a facing surface of the second member facing the first member.

3. The electronic device according to claim 1, wherein the electronic device provides one of three pairs of upper and lower arms of a three-phase inverter, the electronic component is one of semiconductor chips each having one surface and a back surface opposite to the one surface in the stacking direction, the one surface and the back surface being provided with respective electrodes, and the semiconductor chips include an upper-arm chip providing the upper arm and a lower-arm chip providing the lower arm, the upper-arm chip and the lower-arm chip are arranged in an orthogonal direction orthogonal to the stacking direction such that the respective one surfaces of the upper- and lower-arm chips are located on a same side of the upper- and lower-arm chips in the stacking direction, the electronic device further comprising:

a first heat sink and a second heat sink providing a pair of heat sinks disposed such that each of the semiconductor chips is individually interposed between the pair of heat sinks in the stacking direction so as to dissipate heat generated from the semiconductor chip, wherein the first heat sink is disposed adjacent to the one surface of the semiconductor ship in the stacking direction and electrically connected to the electrode on the one surface, the second heat sink is provided by the first member, and the second heat sink is disposed adjacent to the back surface of the semiconductor chip in the stacking direction and includes a main body part electrically connected to the electrode on the back surface and an extending part extending from the main body part in the orthogonal direction; and a joint part and a main terminal which are provided by the second member, disposed closer to the semiconductor chip than the extending part so as to face the extending part in the stacking direction and electrically connected to the extending part via the solder, wherein the joint part is connected to the extending part of one of the upper arm and the lower arm, and the main terminal is connected to the extending part of the other of the upper arm and the lower arm.

4. The electronic device according to claim 1, wherein the first member has a groove part on the facing surface so as to surround the connection region and a protruding part on the back surface to correspond to the groove part and serving as a positional reference part.

5. The electronic device according to claim 4, wherein the uneven oxide film is provided on the positional reference part of the back surface of the first member.

6. The electronic device according to claim 1, wherein the first member has a first groove part on the facing surface so as to surround the connection region and a second groove part on the back surface to correspond to the first groove part and serving as a positional reference part.

7. The electronic device according to claim 1, wherein the uneven oxide film is provided over an entirety of the back surface of the first member.

8. The electronic device according to claim 1, wherein the metal thin film has a plurality of depressed parts in a surface of a portion of the metal thin film where the uneven oxide film is provided.

9. The electronic device according to claim 1, wherein the portion of the metal thin film where the uneven oxide film is provided has an average thickness smaller than an average thickness of a portion of the metal thin film where the uneven oxide film is not provided.

10. A method of manufacturing an electronic device, the electronic device including:

an electronic component;

a sealing resin body sealing the electronic component;

a first member having at least a portion located in the sealing resin body; and a second member connected to the first member via a solder in the sealing resin body, wherein the first member includes a base material formed of a metal material and a coated film provided at least on a surface of the base material which is adjacent to a back surface of the first member opposite to a facing surface of the first member facing the second member, the coated film includes a metal thin film provided on the surface of the base material and an uneven oxide film provided on the metal thin film and made of an oxide of a metal that is a same metal as a main component of the metal thin film, and the uneven oxide film is provided in the back surface of the first member so as to overlap at least an entirety of a connection region of the facing surface of the first member which is connected to the solder in a projected view along a stacking direction in which the first member, the solder, and the second member are stacked, the method comprising:

preparing the base material formed with the metal thin film;

forming the uneven oxide film by irradiating a surface of the metal thin film on the back surface of the first member with a pulse oscillation laser beam, the surface of the metal think film irradiated includes at least a portion that corresponds to an entire region of the connection region;

connecting the first member and the second member via the solder;

after the forming of the uneven oxide film and the connecting of the first member and the second member, molding the sealing resin body; and, after the molding of the sealing resin body, inspecting the solder from a side adjacent to the first member in the stacking direction using a supersonic flaw detector.

* * * * *